(12) United States Patent
Maynard (10) Patent No.: US 12,251,171 B2
(45) Date of Patent: Mar. 18, 2025

(54) SURGICAL ITEM DETECTION SYSTEM FOR IN VIVO FOREIGN OBJECT DETECTION BY MAGNETIC FLUX LEAKAGE

(71) Applicant: Covidien LP, Mansfield, MA (US)

(72) Inventor: Edwin M. Maynard, Frederick, CO (US)

(73) Assignee: Covidien LP, Mansfield, MA (US)

( * ) Notice: Subject to any disclaimer, the term of this patent is extended or adjusted under 35 U.S.C. 154(b) by 146 days.

(21) Appl. No.: 17/966,101

(22) Filed: Oct. 14, 2022

(65) Prior Publication Data

US 2024/0122652 A1  Apr. 18, 2024

(51) Int. Cl.
*A61B 34/20* (2016.01)
*A61B 5/06* (2006.01)

(52) U.S. Cl.
CPC .............. *A61B 34/20* (2016.02); *A61B 5/062* (2013.01); *A61B 2034/2051* (2016.02)

(58) Field of Classification Search
None
See application file for complete search history.

(56) References Cited

U.S. PATENT DOCUMENTS

| | | |
|---|---|---|
| 8,246,547 B2 | 8/2012 | Phua et al. |
| 8,624,588 B2 | 1/2014 | Vig et al. |
| 2017/0235386 A1* | 8/2017 | Almholt ............... H03K 17/955 345/174 |
| 2018/0062071 A1 | 3/2018 | Bolognia et al. |
| 2020/0372409 A1* | 11/2020 | Srivastava ............... G06N 3/08 |
| 2021/0059766 A1* | 3/2021 | Graetzel ............. A61B 90/361 |
| 2021/0113113 A1* | 4/2021 | Weprin .................. G01V 13/00 |
| 2022/0054036 A1 | 2/2022 | Mikhail et al. |

* cited by examiner

*Primary Examiner* — Patricia J Park
(74) *Attorney, Agent, or Firm* — Carter, DeLuca & Farrell LLP (57) ABSTRACT

A detection system for detection of surgical implements within a body of a patient, includes a magnetic field generator configured to generate a magnetic field, a sensor configured to sense a distortion in the magnetic field in response to an approximation of the sensor to a surgical implement, a processor, and a memory. The memory includes instructions stored thereon, which, when executed by the processor, cause the system to: generate a directional magnetic field within a surgical site by the magnetic field generator; sense a distortion in the magnetic field using the sensor; and determine a presence of the surgical implement in response to the sensed distortion in the directional magnetic field.

16 Claims, 9 Drawing Sheets

SURGICAL ITEM DETECTION SYSTEM FOR IN VIVO FOREIGN OBJECT DETECTION BY MAGNETIC FLUX LEAKAGE

FIELD

This disclosure relates generally to detection systems for retained surgical items, and more particularly, foreign object detection by magnetic flux leakage for use within surgical sites.

BACKGROUND

It is often useful to determine whether objects associated with a surgery are present in a patient's body before completion of the surgery. Such objects may take a variety of forms. For example, the objects may take the form of instruments, for instance, scalpels, scissors, forceps, hemostats, and/or clamps. Also, for example, the objects may take the form of related accessories and/or disposable objects, for instance, surgical sponges, gauzes, and/or pads. Failure to locate an object before closing the patient may require additional surgery, and in some instances, may have unintended medical consequences.

Accordingly, there is a need for a technology that is capable of providing the functionality of both presence detection and tagged surgical item/implement identification, while in the medical setting, as well as inventory controls of the tagged items/implements. Specifically, detecting the presence of, identifying, and maintaining inventory of tagged surgical items and materials that are used during the execution of a medical procedure. Technologies exist that enable these functions both individually as well as in conjunction with each other, but the methods and packaging of the discrete solutions used are not ideal for the application. More specifically, the components attached or affixed to the items being tracked may either be too large physically and present nuisances or obstacles in the execution of the procedure, or the detection and identification performance of the solution may degrade rapidly in the presence of variable and uncontrolled dielectric or conductive materials.

Accordingly, there are needs for improvements in presence detection, tagged item identification, and inventory functionality in the medical setting.

SUMMARY

This disclosure relates to systems for detection of surgical objects and devices used in body cavities during surgery.

In accordance with aspects of the disclosure, a detection system for detection of surgical implements within a body of a patient, includes a magnetic field generator configured to generate a magnetic field, a sensor configured to sense a distortion in the magnetic field in response to an approximation of the sensor to a surgical implement, a processor, and a memory. The memory includes instructions stored thereon, which, when executed by the processor, cause the system to: generate a directional magnetic field within a surgical site by the magnetic field generator; sense a distortion in the magnetic field using the sensor; and determine a presence of the surgical implement in response to the sensed distortion in the directional magnetic field.

In an aspect of the present disclosure, the sensor may include a voice coil, a Hall Effect sensor, and/or a tunneling magneto-resistive sensor.

In yet another aspect of the present disclosure, the sensor may be disposed within at least one of a surgical mattress or a wand.

In a further aspect of the present disclosure, the instructions, when executed by the processor, may further cause the system to: provide an indication of the presence of the surgical implement.

In yet a further aspect of the present disclosure, the instructions, when executed by the processor, may further cause the system to: determine a material of the surgical implement based on an amount of distortion sensed by the sensor; and display the material on a display.

In an aspect of the present disclosure, the determining of the material may be performed by providing to a trained machine learning network the sensed distortion and predicting the material by the machine learning network.

In another aspect of the present disclosure, the magnetic field generator may generate an AC magnetic field and/or a DC magnetic field.

In yet another aspect of the present disclosure, the magnetic field generator may include an AC coil and/or a Halbach array.

In a further aspect of the present disclosure, the instructions, when executed by the processor, may further cause the system to: generate a transient magnetic field, induce a residual magnetic field on the surgical implement in response to the transient magnetic field, and sense by the sensor the residual magnetic field of the surgical implement.

In an aspect of the present disclosure, the instructions, when executed by the processor, may further cause the system to perform a presurgical scan to obtain a baseline based on the magnetic field prior to surgery and perform a postsurgical scan to sense the distortion in the magnetic field in response to the surgical implement.

In accordance with aspects of the disclosure, a computer-implemented method for detection of surgical implements within a body of a patient includes generating a directional magnetic field within a surgical site by a magnetic field generator, sensing a distortion in the directional magnetic field using a sensor, and determining a presence of a surgical implement in response to the sensed distortion in the directional magnetic field.

In an aspect of the present disclosure, the sensor may include a voice coil, a Hall Effect sensor, and/or a tunneling magneto-resistive sensor.

In yet another aspect of the present disclosure, the method may further include transmitting information to a display to display information related to the detected surgical implement.

In a further aspect of the present disclosure, the method may further include providing an indication of the presence of the surgical implement.

In yet a further aspect of the present disclosure, the method may further include determining a material of the surgical implement based on an amount of distortion in the directional magnetic field sensed by the sensor and displaying the material on a display.

In an aspect of the present disclosure, the determining the material may be performed by providing to a trained machine learning network the sensed distortion in the directional magnetic field; and predicting the material by the machine learning network.

In another aspect of the present disclosure, the magnetic field generator may generate an AC magnetic field and/or a DC magnetic field.

In yet another aspect of the present disclosure, the magnetic field generator may include an AC coil and/or a pair of permanent magnets In a further aspect of the present disclosure, the method may further include generating a transient magnetic field, inducing a residual magnetic field on the surgical implement in response to the transient magnetic field, and sensing by the sensor the residual magnetic field of the surgical implement.

In accordance with aspects of the disclosure, a non-transitory computer-readable medium containing instructions for executing a computer-implemented method for detection of surgical implements within a body of a patient is presented. The method includes generating a directional magnetic field within a surgical site by a magnetic field generator, sensing a distortion in the directional magnetic field using a tunneling magneto-resistive sensor in response to an approximation of the sensor to a surgical implement, and determining a presence of a surgical implement in response to the sensed distortion in the directional magnetic field.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged or shrunk and positioned to improve drawing legibility. Further, the particular shapes of the elements as drawn are not intended to convey any information regarding the actual shape of the particular elements and have been solely selected for ease of recognition in the drawings.

DETAILED DESCRIPTION

In the following description, certain specific details are set forth in order to provide a thorough understanding of disclosed aspects. However, one skilled in the relevant art will recognize that aspects may be practiced without one or more of these specific details or with other methods, components, materials, etc. In other instances, well-known structures associated with transmitters, receivers, or transceivers have not been shown or described in detail to avoid unnecessarily obscuring descriptions of the aspects.

Reference throughout this specification to "one aspect" or "an aspect" means that a particular feature, structure, or characteristic described in connection with the aspect is included in at least one aspect. Thus, the appearances of the phrases "in one aspect" or "in an aspect" in various places throughout this specification are not necessarily all referring to the same aspect. Furthermore, the particular features, structures, or characteristics may be combined in any suitable manner in one or more aspects.

Figure 1:
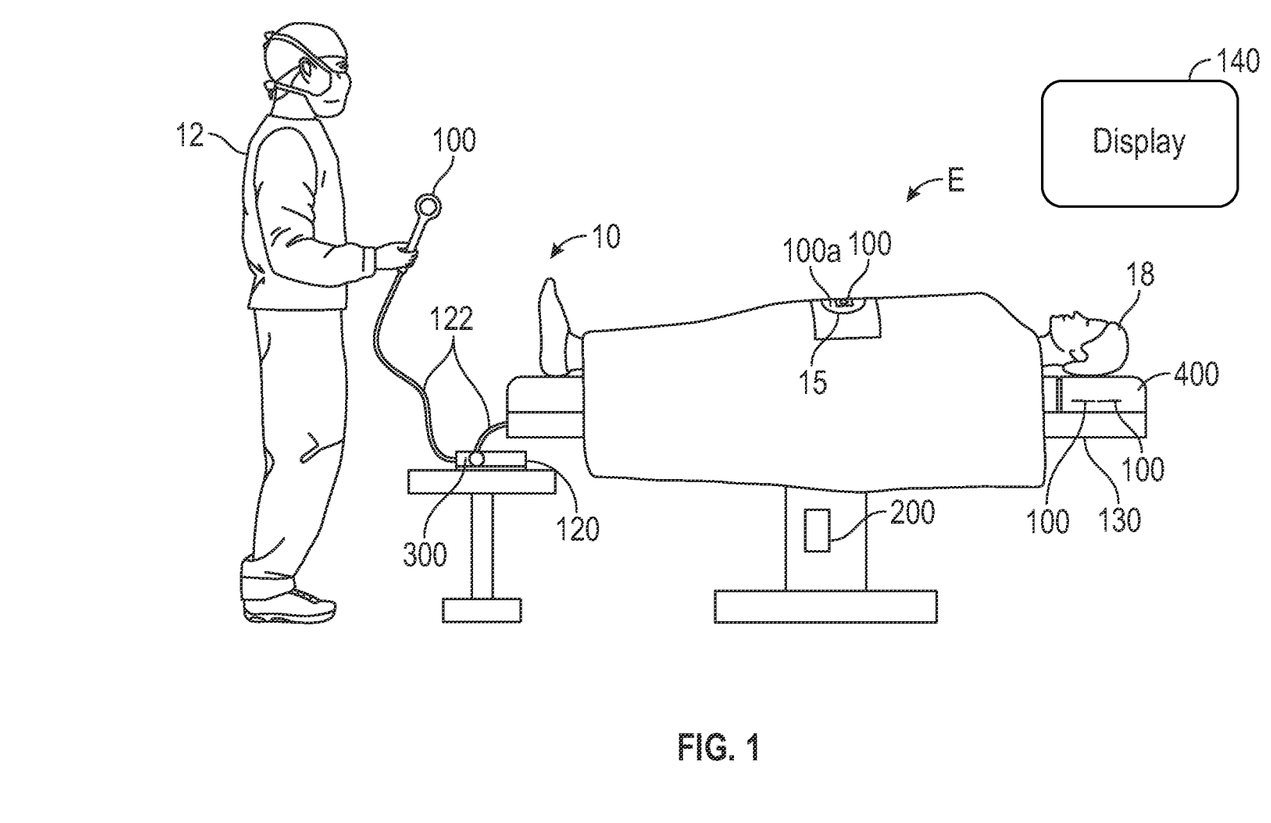
FIG. 1 is a schematic diagram illustrating a detection system configured for detecting an object within a patient according to one illustrated aspect.
Figure 5:
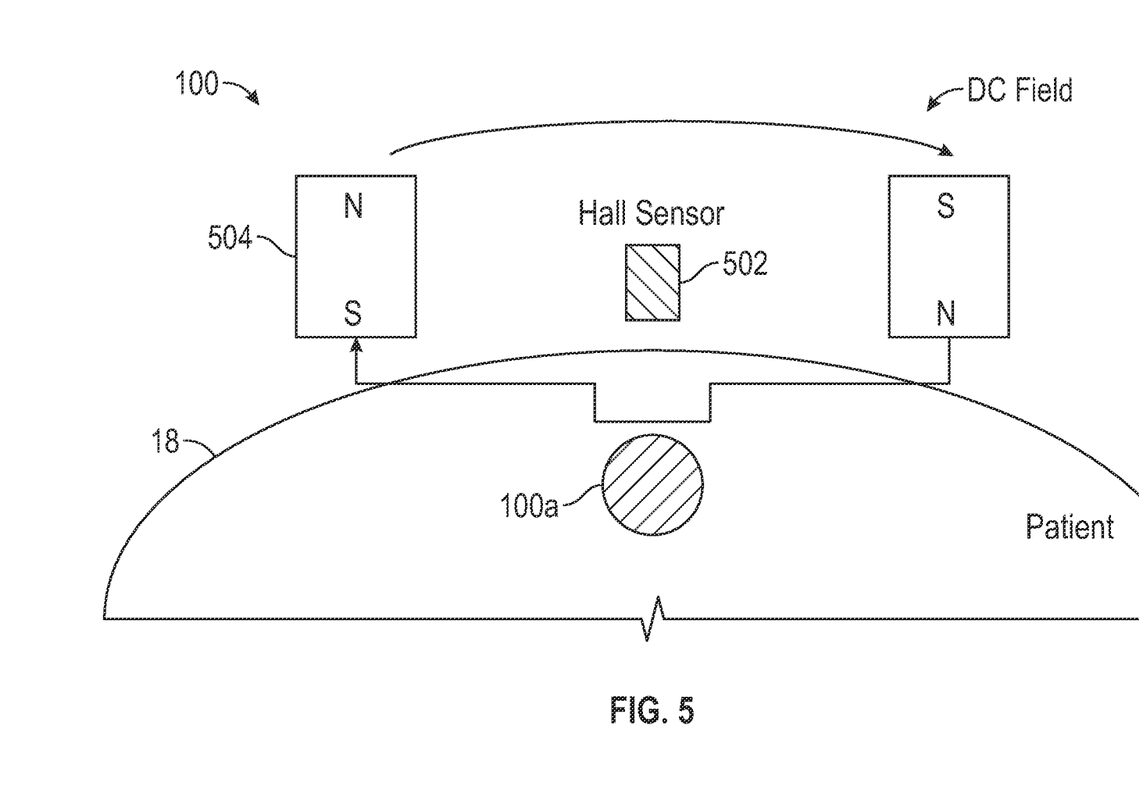
FIG. 5 is a side cutaway view of an antenna with a DC magnetic field for detection of surgical implements within a patient's body in active use within a surgical site in accordance with embodiments of the present disclosure.

FIG. 1 depicts a detection system 10 for the detection of surgical implements or objects 100a in a patient 18. The detection system 10 generally includes antenna 100 that is configured for sensing a change in a magnetic field and a controller 200 coupled to the antenna 100 by one or more communication paths, for example, coaxial cable 122. In one aspect of the detection system 10, the antennae 100 may be embedded in a mattress 400. The antenna 100 generally includes a sensor 502 and a magnetic field generator 504 (FIG. 5). The sensor 502 may include voice coils, Hall Effect sensors, and/or magneto-resistive sensors (e.g., tunnel magneto-resistive (TMR) sensors). TMR sensors provide the benefit of beings approximately 2000× more sensitive than Hall Effect sensors.

The disclosed technology uses the principle of magnetic flux leakage (MFL) to detect magnetic anomalies in patients. Permanent magnets may be used to establish a field that is only slightly influenced by the body. As the field encounters metals, the field distorts (more for ferrous materials, however eddy currents form in any metal due to changing magnetic field). The presence of metal in a non-metallic background (the patient) causes distortion to the magnetic field. The distortion in the magnetic field may include magnetic flux leakage. This works because it is possible to make highly directional magnets (so as to not interact with every piece of metal in the OR setting) and that TMR sensors are able to measure exquisitely subtle changes in the field. Thus, if the sensed magnetic field remains constant, there are no objects present in the surgical site.

The object 100a may take a variety of forms, for example, instruments, accessories, and/or disposable objects useful in performing surgical procedures. For instance, the object 100a may take the form of scalpels, scissors, forceps, hemostats, and/or clamps. Also, for example, the objects 100a may take the form of surgical sponges, gauze, and/or padding. For example, cotton (in the case of a sponge) may be doped so it can be directly detected rather than by using a tag. A benefit of using doped cotton to increase its detectability, is that the doping will not require nanoparticles. Consequently, the sponges do not require high manufacturing tolerances or expensive materials and thus may be inexpensive to manufacture. The disclosed technology provides the benefit that objects as small as needles may be detected. Any object can be made detectable, for example, sutures, by doping the object 100a with a material that induces a distortion in the magnetic field. The disclosed technology further provides the benefit that a special magnetically shielded room does not need to be constructed to use the technology to detect objects 100a.

In use, the medical provider 12 may use the detection system 10 in order to detect the presence or absence of the one or more objects 100a in the patient 18.

The term "read range," as used in this disclosure, includes the distance from an antennae 100 of a detection system 10 and the geometric center of the object 100a (FIG. 1).

In aspects, a signal generator 300 may generate an energizing signal for generating a magnetic field using an AC coil 704 (FIG. 7) as the magnetic field generator 504. The controller 200 may determine whether a distortion in the generated magnetic field marks a surgical implement used in a procedure via the antenna 100. Then the controller may transmit information to a display 140 to display information related to the object 100a.

Figure 2:
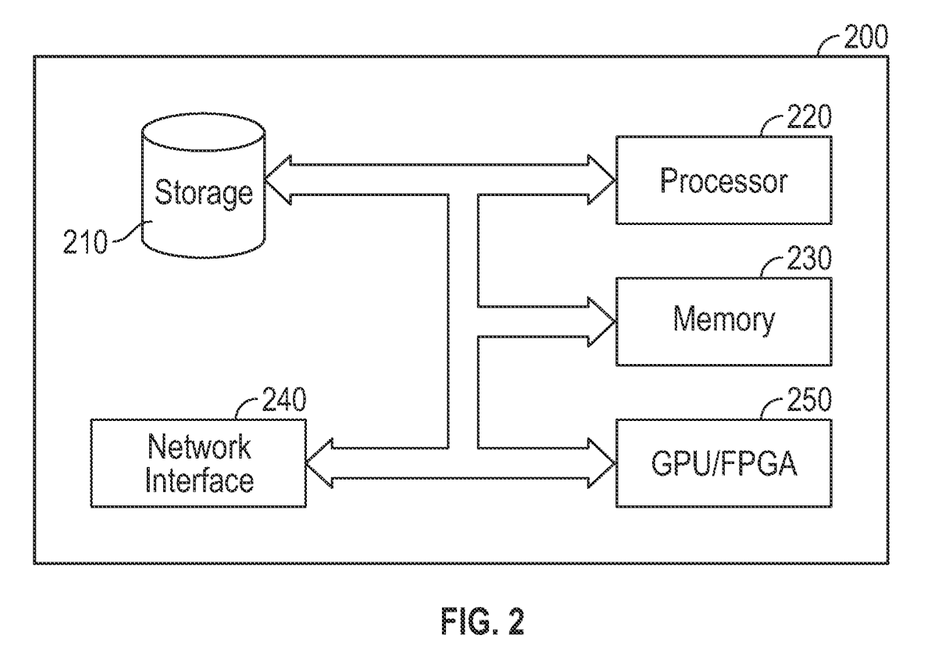
FIG. 2 is a functional block diagram of a controller configured for use with the detection system of FIG. 1 in accordance with embodiments of the present disclosure.

Now referring to FIG. 2, controller 200 includes a processor 220 connected to a computer-readable storage medium or a memory 230. The computer-readable storage medium or memory 230 may be a volatile type of memory, e.g., RAM, or a non-volatile type of memory, e.g., flash media, disk media, etc. In various aspects of the disclosure, the processor 220 may be another type of processor such as a digital signal processor, a microprocessor, an ASIC, a graphics processing unit (GPU), a field-programmable gate array (FPGA), or a central processing unit (CPU). In certain aspects of the disclosure, network inference may also be accomplished in systems that have weights implemented as memristors, chemically, or other inference calculations, as opposed to processors.

In aspects of the disclosure, the memory 230 can be random access memory, read-only memory, magnetic disk memory, solid-state memory, optical disc memory, and/or another type of memory. In some aspects of the disclosure, the memory 230 can be separate from the controller 200 and can communicate with the processor 220 through communication buses of a circuit board and/or through communication cables such as serial ATA cables or other types of cables. The memory 230 includes computer-readable instructions that are executable by the processor 220 to operate the controller 200. In other aspects of the disclosure, the controller 200 may include a network interface 240 to communicate with other computers or to a server. A storage device 210 may be used for storing data. The disclosed method may run on the controller 200 or on a user device, including, for example, on a mobile device, an IoT device, or a server system.

Figure 3:
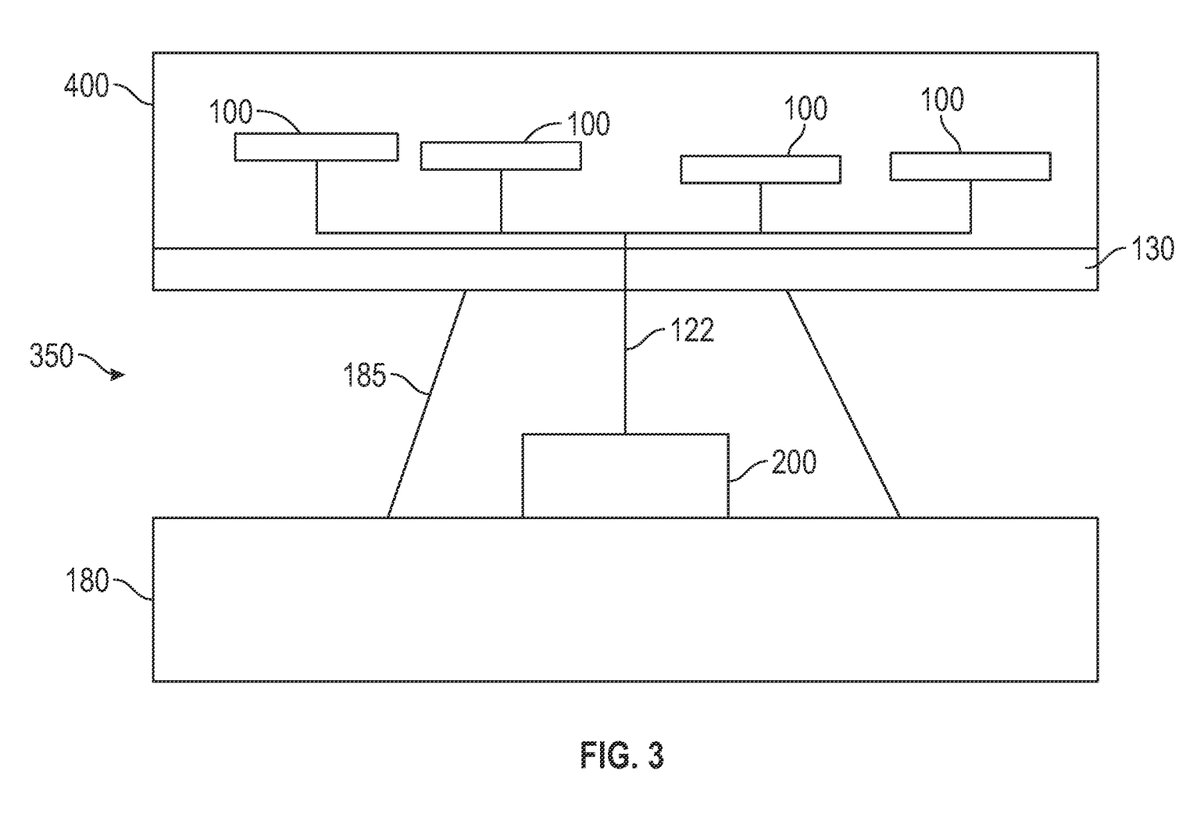
FIGS. 3 and 4 are side cutaway views of surgical tables configured for use with the detection system of FIG. 1 in accordance with embodiments of the present disclosure.
Figure 4:
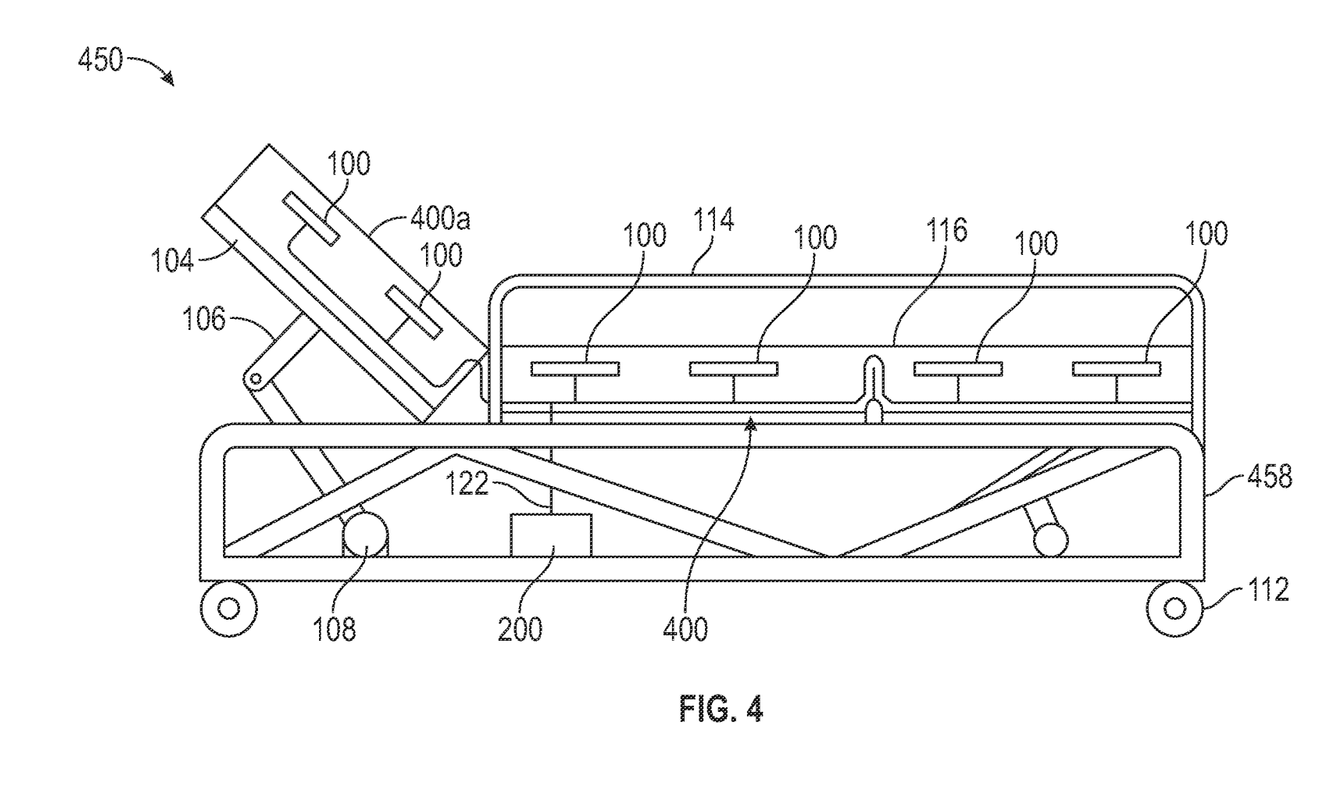

FIGS. 3 and 4 are side cutaway views of surgical tables configured for use with the detection system of FIG. 1.

Referring to FIG. 3, the antenna 100 of the detection system 10 may be carried by the surgical table 350, for example, carried by inner layers of the mattress 130 or positioned in an interior of a shell or housing forming a patient support structure. The controller 200 of the detection system 10 may be positioned in the pedestal or base 180, for example, in an interior of the pedestal or base 180. One or more wired or wireless communication paths may communicatively couple the controller 200 to the antenna 100, and/or to a detection system interface on display 140 (FIG. 1), for example, coaxial cable 122.

The detection system 10 may receive power from a variety of sources, for example, from a wall outlet or receptacle via a conventional power cord and plug (not shown), a battery, or the like.

FIG. 4 shows an environment in which medical procedures are performed that include a bed (e.g., patient bed) 450 and a detection system 10, according to another illustrated embodiment. The aspects of FIG. 4 are similar in some respects to the previously described example, hence only significant differences in structure and operation will be discussed.

The environment may, for example, take the form of a hospital room, clinic room, or examination room of a medical practitioner's office.

The bed 450 may include a patient support structure 104 and a frame or base 458. The patient support structure 104 may support one or more mattresses, for example, a segmented mattress 400. The frame or base 458 may be made of plastic, metal, composite, reinforced composited, and/or roto-molded materials. Various commercially available designs of frames for patient beds are suitable. The frame or base 458 may include a set of wheels 112 (only one called out in FIG. 4), allowing the bed 450 to be easily moved. The frame or base 458 may include one or more rails 114, which may or may not be removable or which may or may not fold down.

The bed 450 may include one or more electric motors 108 and linkages 106, which are selectively actuated to move or articulate portions of the bed 450 or mattress 400. Other mechanisms may be used to move portions of the mattress 400. Commercially available patient or hospital beds 450 typically include one or more pieces of electrical or electronic equipment (e.g., electric motors 108) which are sources of radio noise that may interfere with the detection system 10. Such equipment typically produces very consistent or periodic (i.e., non-random) noise. Some aspects of the detection system 10 discussed herein employ various techniques to address such noise.

In aspects, antenna 100 of the detection system 10 is carried by the patient support structure 104, mattress 400 or frame or base 458. For example, the antenna 100 may be carried by inner layers of the mattress 400 or positioned in an interior of a shell or housing forming the patient support structure 104. While illustrated as being in non-overlapping relationship, in some aspects more than one antenna 100 may overlap. A controller 200 of the detection system 10 may be carried by the frame or base 458. One or more wired or wireless communication paths may communicatively couple the controller 200 to the antenna 100 and/or to a detection system interface, for example, coaxial cable 122.

Referring to FIG. 5, an antenna 100 for detecting surgical implements in a surgical site based on magnetic flux leakage is shown. The antenna 100 includes a sensor 502 (e.g., a hall effect sensor) configured to generate a signal in response to a changing magnetic field, a magnetic field generator 504 (e.g., a pair of permanent magnets arranged in a polar opposite configuration), and a controller 200 (FIG. 1) configured to receive and process the signal. The magnetic field generator 504 is configured to generate a DC magnetic field. A DC magnetic field is a constant magnetic field that does not oscillate at a frequency. For DC magnetic fields, there is a constant attraction between negative and positive poles of the magnet. The magnetic field generator 504 may include a Halbach array. A Halbach array is an arrangement of permanent magnets that augments the magnetic field on one side of the array while cancelling or reducing the magnetic field to near zero on the other side of the array.

The sensor 502 is configured to sense changes in a flux strength as a metal object (e.g., a surgical implement) forces some flux outside of the object. The sensor 502 is configured to communicate the sensed change in flux strength (e.g., flux leakage) to the controller 200 for processing. For example, the background flux of the magnetic field generated by magnetic field generator 504 changes as metal distorts the magnetic field. The sensor 502 senses the change in the flux and communicates the sensed change to the controller 200. The controller 200 may provide an indication of the detection of an object. For example, the controller 200 may display on a display 140 (FIG. 1) that an object was detected.

Figure 6:
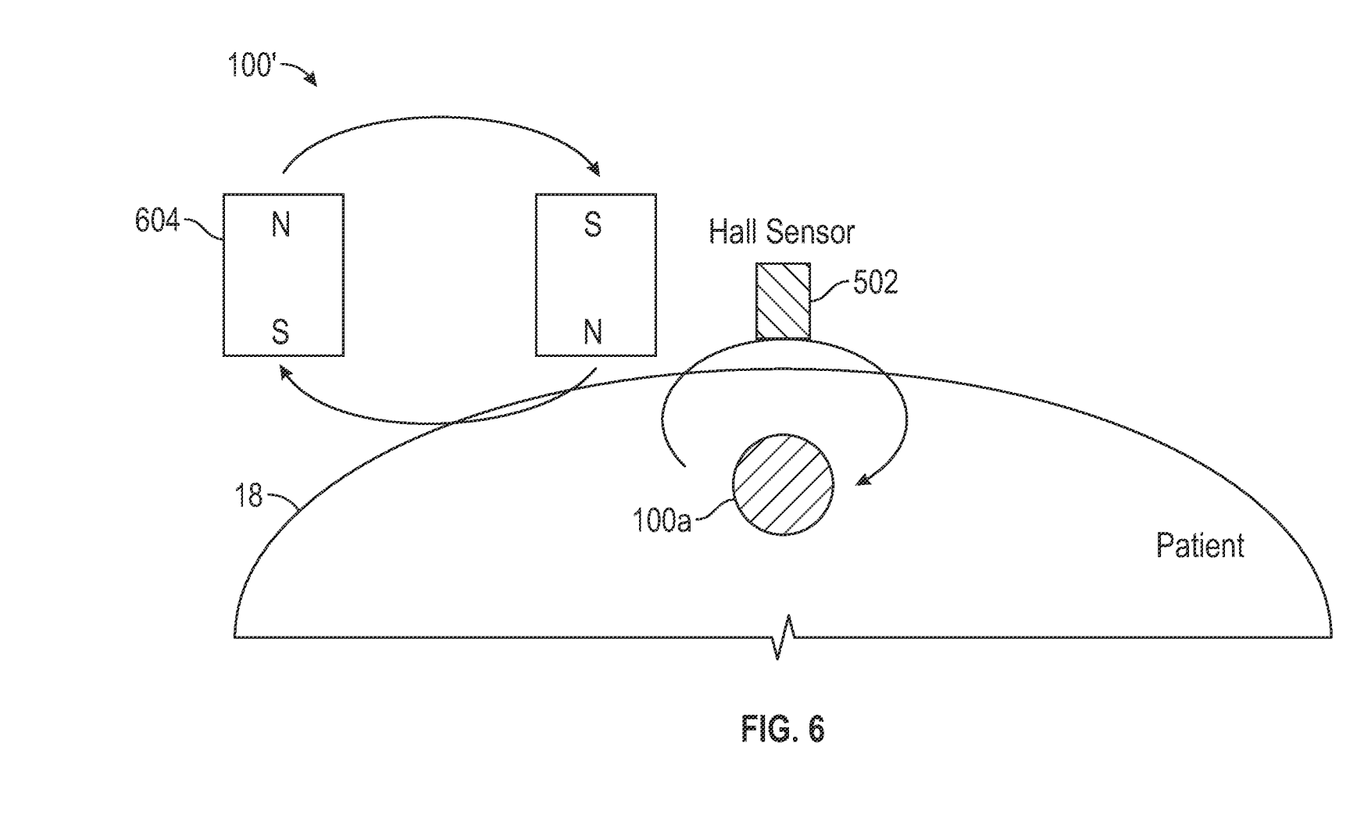
FIG. 6 is a side cutaway view of an antenna with a transient magnetic field for detection of surgical implements within a patient's body in active use within a surgical site in accordance with embodiments of the present disclosure.

Referring to FIG. 6, an antenna 100' for detecting surgical implements in a surgical site based on magnetic flux leakage is shown. A transient magnetic field may be generated that induces a residual magnetic field in the object 100a. The residual magnetic field is sensed by the sensor 502. The sensed signal is communicated by the sensor 502 to the controller 200 for processing. For example, the magnetic field generator 604 (e.g., a Halbach array) may be waived across a patient 18. A residual magnetic field is induced on any metal objects 100a (or doped objects) within the patient 18. The sensor 502 may then detect the residual magnetic field in the object 100a and communicate a signal to the controller 200 indicating that an object 100a is detected.

Figure 7:
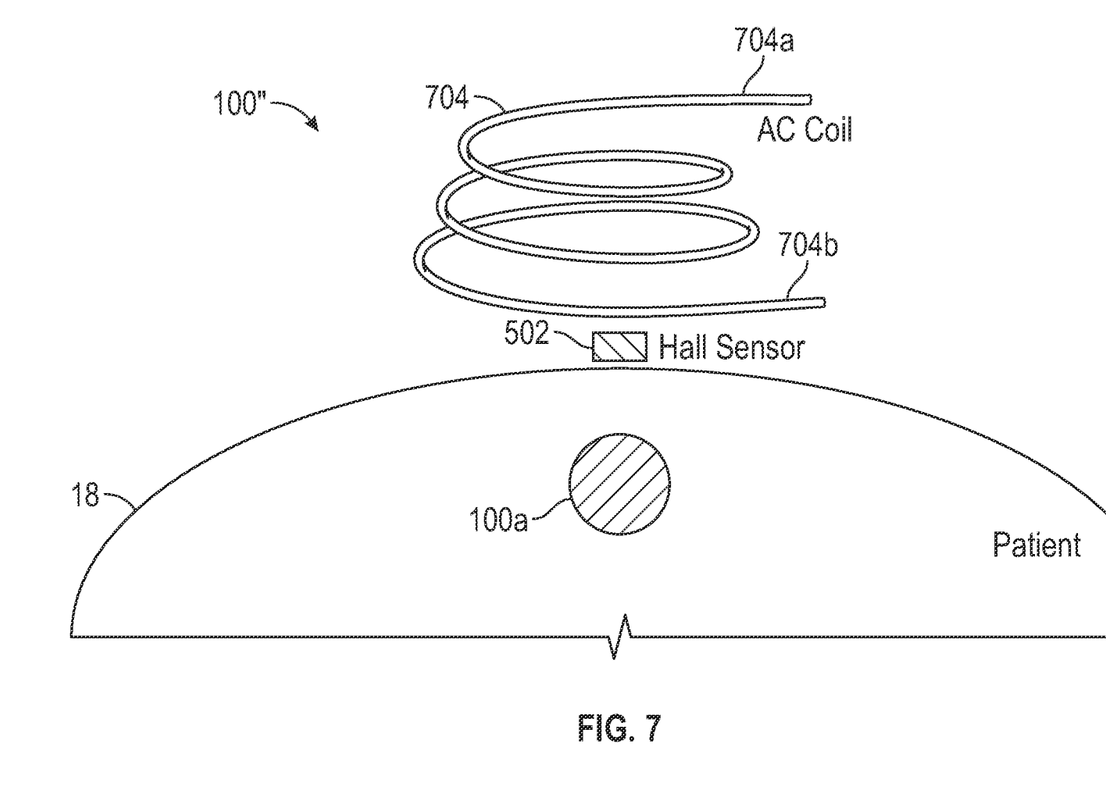
FIG. 7 is a side cutaway view of an antenna with an AC magnetic field for detection of surgical implements within a patient's body in active use within a surgical site in accordance with embodiments of the present disclosure.

FIG. 7 shows an antenna 100" for detecting surgical implements in a surgical site based on magnetic flux leakage. The antenna 100" includes a sensor 502 (e.g., a TMR sensor) configured to generate a signal in response to a changing magnetic field, an AC coil 704 connected to a generator (such as generator 300) by terminals 704a, 704b and configured to generate an AC magnetic field, and a controller 200 (FIG. 1), configured to receive and process the signal. An AC magnetic field is a magnetic field that oscillates at a frequency. The AC magnetic field generated by AC coil 704 induces eddy currents in the metal of object 100a, which is picked up by sensor 502. The sensed signal is communicated by the sensor 502 to the controller 200 for processing.

Figure 8:
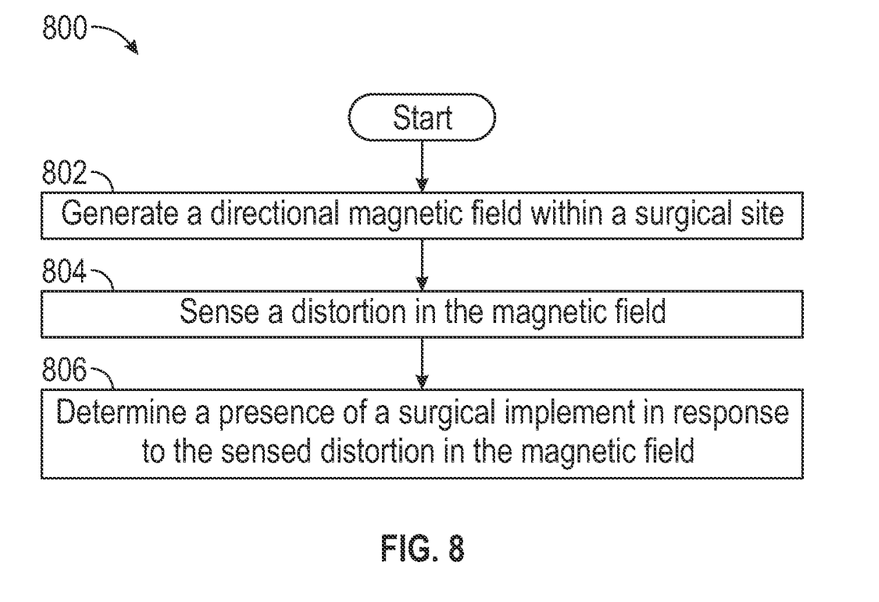
FIG. 8 is a flow diagram of a computer-implemented method for detecting surgical implements in a surgical site, in accordance with aspects of the present disclosure.

Referring to FIG. 8, a flow diagram for an operation 800 in accordance with aspects of the present disclosure for detecting surgical implements in a surgical site is shown. Although the blocks of FIG. 8 are shown in a particular order, the blocks or steps need not all be performed in the illustrated order, and certain blocks can be performed in another order. The operation of FIG. 8 will be described below, and such operation may be performed by the system 10 of FIG. 1. In aspects, the operations or steps of FIG. 8 and/or other disclosed operations or steps may be performed all, or in part, by another device, for example, a server, a central system, a cloud system a user device, and/or a computer system, among others. These variations are contemplated to be within the scope of the present disclosure.

At block 802, operation 800 includes the controller 200 generating a directional magnetic field within a surgical site by a magnetic field generator 504. The magnetic field generator 504 may include permanent magnets configured to generate a DC magnetic field or an AC coil configured to generate an AC magnetic field.

At block 804, operation 800 includes the controller 200 sensing a distortion in the magnetic field using the sensor 502 (e.g., a TMR sensor). For example, the background magnetic flux may change as metal distorts the DC magnetic field (FIG. 5). The sensor 502 may be disposed within a surgical mattress, a surgical table, and/or an antenna 100 (e.g., a handheld wand). The wand 100 may be waived over the patient 18.

At block 806, operation 800 includes the controller 200 determining a presence of the surgical implement in response to the sensed distortion in the magnetic field. The controller 200 may provide an indication of the presence of the surgical implement. For example, the controller 200 may display on a display (not shown) that an object 100a was detected, sound an audio alert, and/or flash an indicator light.

In aspects, operation 800 may include the controller 200 performing a presurgical scan to obtain a baseline based on the magnetic field prior to surgery. Operation 800 may also include the controller 200 then performing a postsurgical scan to sense the distortion in the magnetic field and compare the results of the presurgical scan to the postsurgical scan to determine if an object 100a is present in the surgical site.

In aspects, operation 800 may include the controller 200 determining a material of the surgical implement based on an amount of distortion sensed by the sensor 502. For example, if the magnetic field distorts by a certain range, the controller 200 may compare the amount of distortion to a table to determine the material of the object 100a. The operation 800 may then include controller 200 displaying on a display (not shown) the determined material. In aspects, the determining of the material may be performed by providing to a trained machine learning network the sensed distortion. The operation may predict the material by the machine learning network, for example a convolutional neural network.

Figure 9:
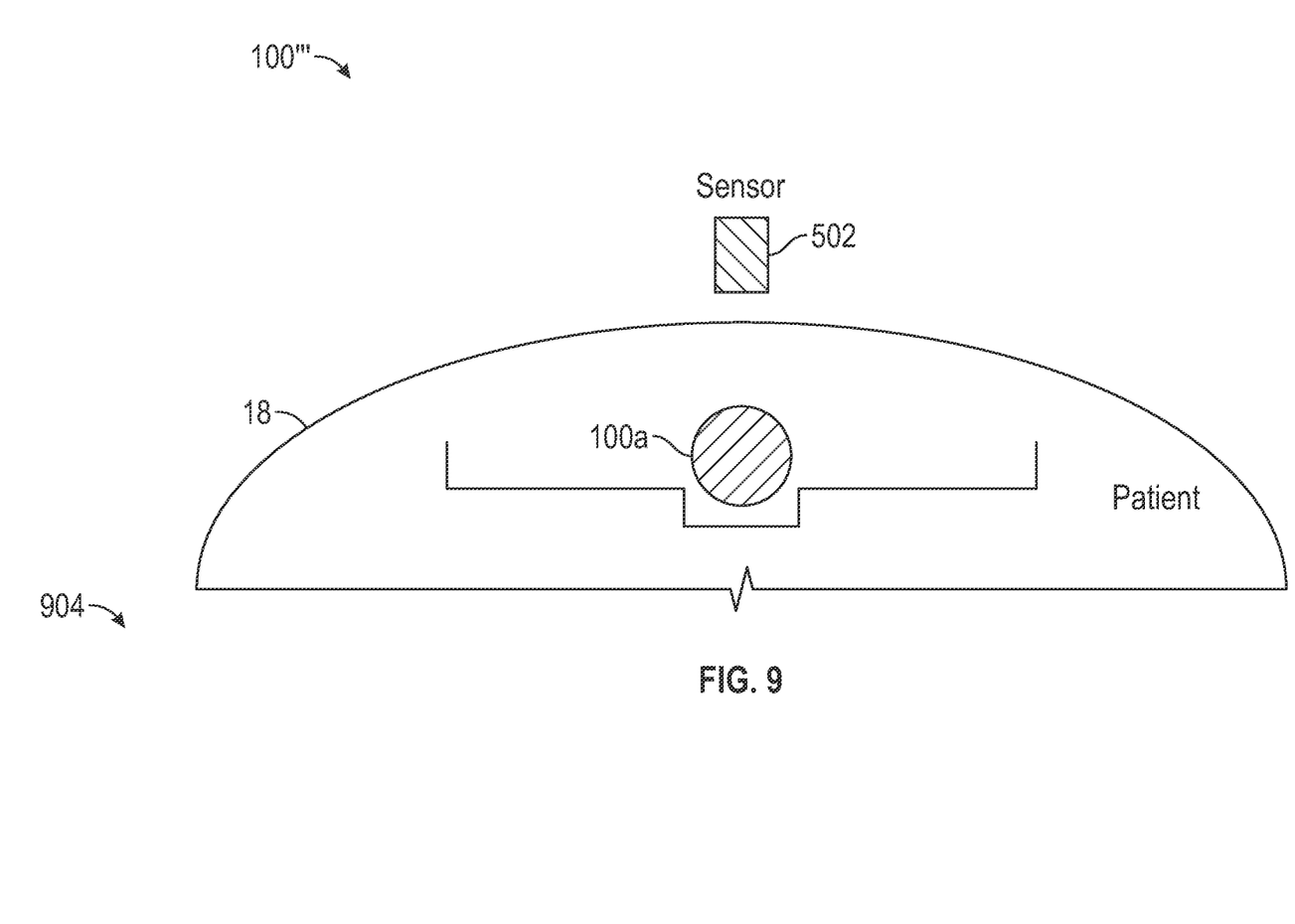
FIG. 9 is a side cutaway view of an antenna with a geomagnetic field for detection of surgical implements within a patient's body in active use within a surgical site in accordance with embodiments of the present disclosure.

Referring to FIG. 9, an antenna 100''' for detecting surgical implements in a surgical site based on flux leakage is shown. The antenna 100''' may utilize a geomagnetic field 904 to detect the object 100a. The geomagnetic field 904 is sensed by the sensor 502. The sensed signal is communicated by the sensor 502 to the controller 200 for processing. The objects 100a within the patient 18 cause a distortion in the geomagnetic field. The sensor 502 may then detect the distortion in the geomagnetic field due to the object 100a and communicate a signal to the controller 200 indicating that an object 100a is detected.

While aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A detection system for detection of a surgical implement within a body of a patient, the detection system comprising:
   a magnetic field generator configured to generate a magnetic field;
   a tunneling magneto-resistive sensor configured to sense a distortion in the magnetic field in response to an approximation of the sensor to the surgical implement;
   a processor; and
   a memory including instructions stored thereon, which, when executed by the processor, cause the system to:
      generate a transient magnetic field;
      induce a residual magnetic field on the surgical implement in response to the transient magnetic field; and
      sense by the sensor the residual magnetic field of the surgical implement.

2. The system of claim 1, wherein the sensor is disposed within at least one of a surgical mattress or a wand.

3. The system of claim 1, wherein the instructions, when executed by the processor, further cause the system to:
   provide an indication of the presence of the surgical implement.

4. The system of claim 1, wherein the instructions, when executed by the processor, further cause the system to:

determine a material of the surgical implement based on an amount of distortion sensed by the sensor; and display the material on a display.

5. The system of claim 4, wherein the determining of the material is performed by providing to a trained machine learning network the sensed distortion; and predicting the material by the machine learning network.

6. The system of claim 1, wherein the magnetic field generator generates at least one of an AC magnetic field or a DC magnetic field.

7. The system of claim 1, wherein the magnetic field generator includes at least one of an AC coil or a Halbach array.

8. The system of claim 1, wherein the instructions, when executed by the processor, further cause the system to:

perform a presurgical scan to obtain a baseline based on the magnetic field prior to surgery; and perform a postsurgical scan to sense the distortion in the magnetic field in response to the surgical implement.

9. A computer-implemented method for detection of a surgical implement within a body of a patient, the method comprising:

generating a transient magnetic field;

inducing a residual magnetic field on the surgical implement in response to the transient magnetic field; and sensing by a tunneling magneto-resistive sensor the residual magnetic field of the surgical implement; and determining a presence of the surgical implement in response to the sensed residual magnetic field.

10. The computer-implemented method of claim 9, further comprising:

transmitting information to a display to display information related to the detected surgical implement.

11. The computer-implemented method of claim 9, further comprising:

providing an indication of the presence of the surgical implement.

12. The computer-implemented method of claim 9, further comprising:

determining a material of the surgical implement based on an amount of distortion in the directional magnetic field sensed by the sensor; and displaying the material on a display.

13. The computer-implemented method of claim 12, wherein the determining the material is performed by providing to a trained machine learning network the sensed distortion in the directional magnetic field; and predicting the material by the machine learning network.

14. The computer-implemented method of claim 9, wherein the magnetic field generator generates at least one of an AC magnetic field or a DC magnetic field.

15. The computer-implemented method of claim 9, wherein the magnetic field generator includes at least one of an AC coil or a pair of permanent magnets.

16. A non-transitory computer-readable medium containing instructions for executing a computer-implemented method for detection of a surgical implement within a body of a patient, the method comprising:

generating a transient magnetic field within a surgical site, by a magnetic field generator;

inducing a residual magnetic field on the surgical implement in response to the transient magnetic field;

sensing by a tunneling magneto-resistive sensor the residual magnetic field of the surgical implement; and determining a presence of the surgical implement in response to the sensed residual magnetic field.

* * * * *